United States Patent [19]

Jones

[11] Patent Number: 4,842,588
[45] Date of Patent: Jun. 27, 1989

[54] METHOD OF LOADING AND DISCHARGING A DRIP CHAMBER

[75] Inventor: J. Paul Jones, Chester Springs, Pa.

[73] Assignee: PRD Corporation, Exton, Pa.

[21] Appl. No.: 151,117

[22] Filed: Feb. 1, 1988

Related U.S. Application Data

[60] Continuation of Ser. No. 51,521, May 19, 1987, abandoned, Division of Ser. No. 836,503, Mar. 5, 1986, Pat. No. 4,685,912.

[51] Int. Cl.$^4$ .............................................. A61M 5/16
[52] U.S. Cl. ..................................... 604/51; 604/126; 604/251
[58] Field of Search ............................... 604/251–255, 604/122, 126, 51

[56] References Cited

U.S. PATENT DOCUMENTS

| | | | |
|---|---|---|---|
| 2,648,333 | 8/1953 | Cutter | 604/251 |
| 2,729,212 | 1/1956 | Butler | 604/251 |
| 2,786,467 | 3/1957 | Price | 604/255 |
| 2,844,147 | 7/1958 | Beacham | 604/254 |
| 2,879,784 | 3/1959 | Cutter | 604/254 |
| 3,030,954 | 4/1962 | Thornton, Jr. | 604/251 |
| 4,009,714 | 3/1977 | Hammer | 604/126 |
| 4,173,222 | 11/1979 | Muetterties | 604/126 |

Primary Examiner—Dalton L. Truluck
Assistant Examiner—Denise Whelton

[57] ABSTRACT

A flexible tube is mounted on top of the drip chamber. The top of the tube is connected to the spike via a one-way ball-type valve. The bottom of the tube is connected to the drip chamber via a duck-bill-type valve inside of the drip chamber. The duck-bill is held closed against head pressure by a metal spring clip acting on the lip. The duck-bill will open when the tube is squeezed and fluid will be injected into the drip chamber.

The drip chamber is charged bubble-free by the use of an output tube open to the chamber and joined to the flexible tubing carrying the hypodermic needle. During the initial fill the output tube is positioned above the fluid level and air in the chamber vented via the output tube, the flexible tubing and the hypodermic needle. When the desired level is reached, the output tube is submerged and bubble-free fluid fills the output tube, the flexible tubing, and the hypodermic needle.

1 Claim, 2 Drawing Sheets

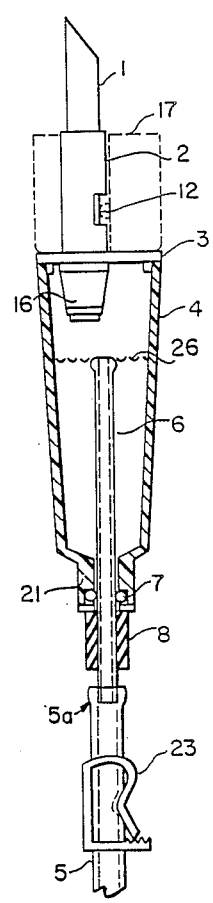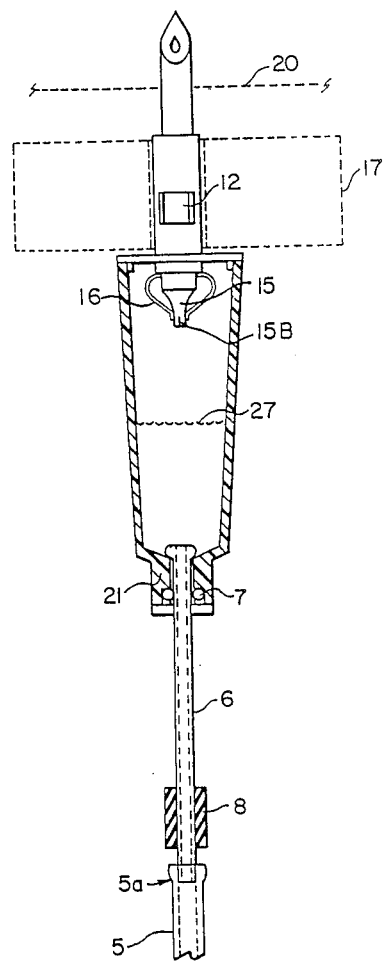
FIG. IA
FIG. IB

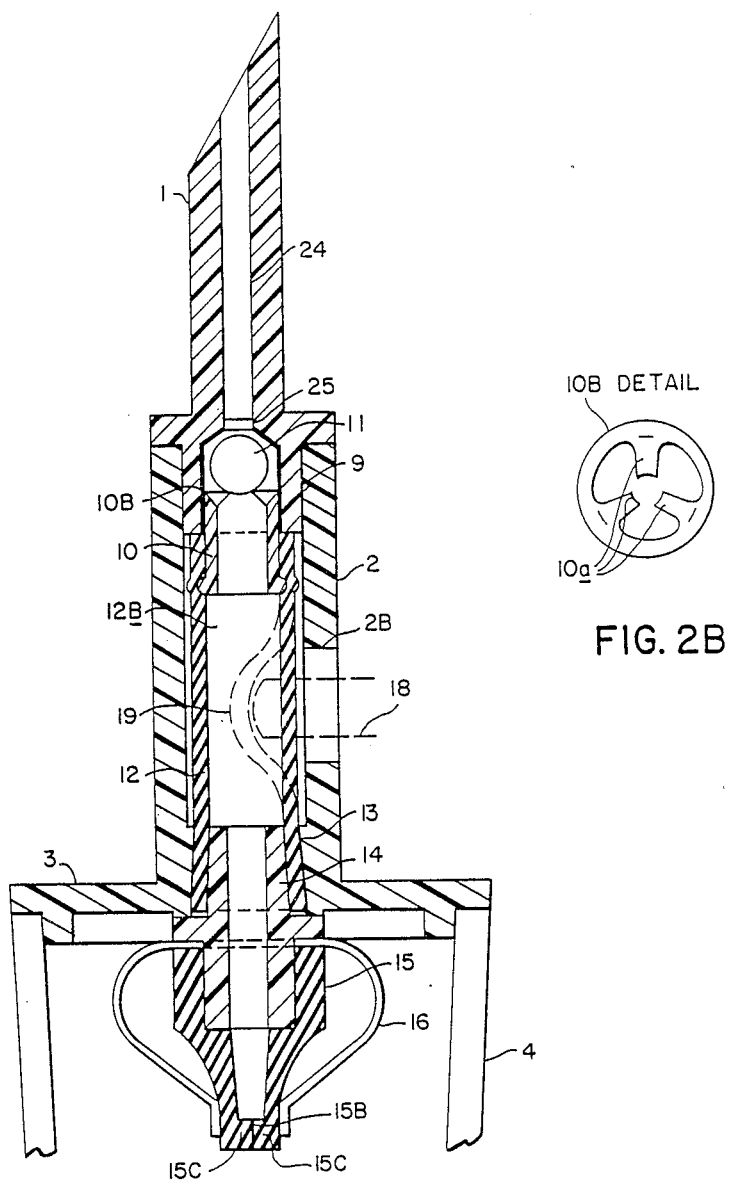

METHOD OF LOADING AND DISCHARGING A DRIP CHAMBER

This application is a continuation of my copending application Ser. No. 051,521 filed 5/19/87, now abandoned, which is a division of my application Ser. No. 836,503 filed 3/5/86, now U.S. Pat. No. 4,685,912.

This invention relates in general to drip chambers for intravenous infusion systems and in particular relates to a pump for injecting drops into the drip chamber and to a method and means for making the initial fill of the chamber, PVC tubing, and hypodermic needle bubble free.

Ordinary intravenous I.V. infusion sets are basically made up of three parts: (1) a spike which is inserted in the bottom of a suspended fluid source; (2) a cylindrical transparent drip chamber which receives the drops from a small aperture in the spike; and (3) a length of flexible PVC tubing which connects the drip chamber to the needle which is inserted into the vein of the patient. There is, in addition, a variable clamp on the PVC tubing which squeezes the tubing to cause a constriction in the fluid flow.

As simple as these basic elements may seem, there is a complicated interrelation between: (1) the height of the "head" of the fluid source above the drop aperture; (2) the size of the drop aperture; (3) the amount of low pressure or suction initially set up by the fluid level in the chamber; (4) the total height of the drip chamber above the patient which determines the syphon effect of the fluid in the tubing; and (5) the resistance to the flow set up by the constricting clamp on the PVC tubing.

All of these factors in combination, or any one of them alone, can affect the drop rate into the chamber and/or the size of the drop. To make matters worse, the drop size and rate can also be affected by the viscosity and temperature of some fluids.

Perhaps the most troublesome of the listed variables is the conventional adjustment clamp which can change its setting as much as 100% in 15 minutes because of the slow rate of change of the set in the PVC tubing when the clamp is tightened or loosened. There are more precision constricting valves which are made to be inserted in series with the tubing. These series control valves can add some precision for additional cost, but all of the other variables mentioned still remain.

It is, therefore, one object of this invention to provide an inexpensive drip chamber which can be controlled with a small clip-on actuator and which, by its design, can set the exact rate of fluid flow (i.e. drop size and rate) while eliminating the variables of: (1) fluid head height; (2) drop aperture; (3) setting up fluid level; (4) the effect of chamber height; and (5) the instability of the variable clamp. The danger of 'flow through' (i.e. when all of the fluid runs out of the tube carrying air into the patient's vein) which can occur in the design of some controllers, is eliminated by the invention since the impulse pump on the drip chamber is normally cut off between electrical impulses from the associated control unit.

Another undesirable characteristic of conventional I.V. systems is that of making the initial fill of the drip chamber and connected PVC tubing and hypodermic needle bubble-free so air cannot be injected into the patient. It is another object of the invention to provide a method and means for a bubble-free initial fill.

The invention will be described below in connection with the following drawings wherein:

FIG. 1A is an elevational view partially in section illustrating an intervenous infusion system drip chamber incorporating my invention;

FIG. 1B is another elevational view partially in section of the drip chamber of FIG. 1A;

FIG. 2A is an enlarged fragmentary view of the top part of FIG. 1A and illustrating drip pump; and FIG. 2B is a plan view of a component of the pump of FIG. 2A.

With reference to FIGS. 1A and 1B, the impulse controlled drip chamber (4) is shown actual size with the dotted lines showing the approximate size of the associated impulse actuator (17) which clamps on to the top of the drip chamber assembly around the square periphery of a hollow rigid extension (2). The impulse actuator (17) is, therefore, no larger than the drip chamber itself, and is located just under the fluid source (20); and is entirely supported by the chamber.

The spike (1) is used to pierce the elastomer seal on the fluid source (20), and the frictional fit will easily support the entire drip chamber assembly and impulse actuator (17).

The spike (1) is welded into the square extension (2) and is connected to the top section (3) of the drip chamber.

There is a vertically movable output tube (6) which is normally extended into the drip chamber (4) until stopped by an abutment in the form of the elastomer finger grip (8) or in the form of the enlarged head 5a. The height that the output tube (6) extends initially into the drip chamber (4) determines the initial fill height of the fluid (26) and the stem (6) is designed to release the air pressure build-up in the chamber (4) while it is initially being filled with fluid to its top level (26) as shown in FIG. 1A. The release of air is through the tube (6), the flexible tubing (5), and the hypodermic needle (not shown) connected thereto.

In FIG. 1B the output tube (6), which is sealed by the O-ring (7), has been drawn down to the bottom of the chamber (21) which allows the output tube (6), the flexible tube (5), and hypodermic needle to quickly fill, without intermittant breaks or bubbles. When the tubes (5) and (6) have been fully filled and fluid is running out of the hypodermic needle, the fluid in the chamber (4) will be stabilized to the new lower level (27) because of the partial vacuum (suction) created by the weight of the water column in the tubes (5) and (6). Then the auxillary cut-off clamp (23) can be used to totally fix the fluid in the tubes (5) and (6) and injection of hypodermic needle until the needle is inserted into the patient. The fluid in the tubes (5) and (6) and in the hypodermic needle will be without bubbles.

This simple set-up procedure is designed to circumvent a presently tedious set-up process which requires trained I.V. crews. The new invention is designed to make the use of the chamber 'fool proof' enough to be used by non-specialist attendants in both hospital and home care environments.

With reference to the expanded drawing, FIG. 2A, the spike (1) has a fluid aperture or passageway (24) which has a small spherical valve seat (25) that mates with a plastic ball valve (11). This ball in practice is 0.125 inches in diameter. The spike base (9) has a small cylindrical insert (10) which has a valve aperture pattern (see FIG. 2B) which allows the fluid to pass, but has fingers (10a) which retain the plastic ball valve (11)

loosely, with a 0.015 gap from the valve seat (25). The insert (10) is hollow and forms part of the passageway (24).

An elastomer tube (12) is frictionally retained on the spike insert (10) at the top, and is pressure-sealed at the bottom end by the valve plug (14) in the aperture (13) of the top plate (3). This tube (12) thereby forms a sealed inner chamber 12b that is terminated by a "duck bill" type check valve (15) at the bottom which is retained by friction on the valve plug (14). The duck bill valve (15) has an exit slot ((15B) which forms the valve opening.

A spring stainless steel pressure clip (16) maintains closing pressure (i.e. enough to resist the maximum fluid head pressure above, on the lips (15C) of the valve opening (15B). The combination of the plastic elastomer valve (15) and external pressure clip (16) provides a unique valve, with unfatigable pressure provided by the metal spring clip which in turn is not exposed to the fluid in passage. This feature is an important part of the invention.

Notice that the elastomer tube (12) is shown in a position by dotted lines (19) wherein it has been depressed by an external actuator or probe (18) that is allowed to enter through the wall of the outer cylinder (2) through the aperture (2B).

It has been found that the uniform depression of the tube in terms of depth and width of the probe (18) displaces a very uniform volume of fluid in the tube (12 which is relatively independent of such production variables as the tube wall thickness, tube length, etc.

As soon as the probe (18) begins to depress the tube wall to the position (19) part of the fluid in the tube moves up to cause the plastic ball valve (11) to instantly rest against the valve seat (25) and prevent any upward flow of the displaced volume of fluid. The otherpart of fluid displaced by the tube at position (19) can only go out the check valve (15) by overcoming the holding pressure of the spring clip (16). It will be apparent that each time the probe or actuator (18) is operated the same volume of fluid is passed through the check valve (15) to the drip chamber.

When the probe (18) is retracted, the elastomer (for example silicone) tube quickly resets to its normal round shape, thereby allowing new fluid to flow down through the ball valve (11) aided by the head pressure from the fluid source above.

The pumping action has thereby been added to a relatively standard I.V. drip chamber with only four small and inexpensive parts. These extra parts include the plastic ball (11), the small section of elastomer tubing (12), the elastomer check valve (15), and the check valve clip spring (16). As is conventional in I.V. systems, all of the parts are plastic (so as to avoid metal contact with the fluid) except the spring clip (16) which is metal but not contactable by the fluid in the check valve (15) nor the fluid exiting through opening (15B).

Before closing I want to point out several important characteristics of the invention. This is done in paragraphs (A) through (G) below.

(A)

A drip chamber including a cap on the top thereof which has a hollow cylindrical extension and a tapered hole in the cap to receive the lower end of the contained section of flexible tubing and a tapered compression plug; a connection spike with a center aperture which is fused to the top of the hollow cylindrical extension and is used to pierce the seal of the fluid source; a plastic ball located below a conforming seat around the edge of the center aperture at the base of the connection spike; a hollow plug which has radial extensions at the top that limit the vertical travel of the plastic ball when the plug is mounted in a hollow cylindrical extension at the base of the spike; a section of flexible tubing which is compression mounted at the top end on an extension of the hollow plug and has its lower end compression sealed by the tapered compression plug; a flexible 'duck bill'-type output check valve which is mounted on a tubular extension of the compression plug in the chamber cap; a metallic spring clip which is retained by the mounting of the flexible check valve and the opposing fingers which press against opposite sides of the valve lips to control the release pressure of the valve.

(B)

An aperture in the side of the hollow cylindrical extension of the drip chamber cap which exposes the centrally located section of flexible tubing which conducts the I.V. fluid from the spike aperture, past the ball valve, and down to the pressure controlled output check valve.

(C)

An aperture in the side of the cylindrical extension of the drip chamber cap admits a reciprocating finger that compresses the contained section of flexible tubing to eject a measured amount of fluid through the pressure controlled output check valve such reciprocating finger being driven by an external means that is normally off and provides a single reciprocating motion for each control impulse applied.

(D)

The spring clip on the flexible output check valve has the design feature of being presettable to a pressure level that will overcome the maximum vertical head pressure from the fluid source and the additional feature of not being exposed to the I.V. fluid that is passing through the output check valve, the pressure setting being established by the thickness of the metal used in the pear-shaped design of the clip and/or the tension formed into the gap between the clip ends before the lips of the flexible check valve are inserted.

(E)

A concentric space around the section of flexible tubing located within the hollow extension of the drip chamber cap is made large enough to allow the flexible tubing to freely expand in width when it is compressed and deformed by the reciprocating finger from an external actuation means such free expansion space being necessary to keep the volume of fluid displaced by the actuator regulated primarily by the uniform size and movement of the actuator finger and not seriously affected by small variations of the outside O.D. of the flexible tubing.

(F)

The design and assembly method of the tapered compression plug in the bottom of the section of flexible tubing and the tapered hole in the cap of the drip chamber mounts the flexible tubing in a condition of mild compression between its two ends, such compression overcoming any tendency for the flexible tubing to move on the hollow plug extension at the base of the spike or in the compression fitting in the cap of the chamber when the flexible tubing is being deformed by the actuator finger extending through the aperture in the side of the hollow cylindrical extension of the chamber cap.

(G)

A vertically movable output tube in the O-ring sealed base of the drip chamber which is connected to the I.V. tubing to the needle and which is designed to such a length that when fully inserted into the chamber at the start of filling, it allows the trapped air to escape from the non-vented chamber and gauges the amount of fluid that should be initially moved into the chamber by a rapid fill control, such gauged fluid level also calculated to rapidly fill the I.V. tube to the needle with fluid without trapped air bubbles when the constrained tube is moved downward to the bottom of the initial fluid level in the chamber with the final level of fluid in the chamber being established by the filling of the I.V. tube and the resulting partial vacuum in the chamber which will prevent excess fluid form running out of the I.V. tubing (called feed-through) when the insertion of controlled drops is stopped.

I claim:

1. A method of loading and discharging a drip chamber in an intravenous infusion system including a source of fluid, a drip chamber, control means, a hypodermic needle, and a flexible tube connecting the needle to the drip chamber, comprising the steps of:
   (a) operating said control means to cause drops of fluid from said source to enter the drip chamber;
   (b) while said drops are entering the drip chamber operating said control means to simultaneously vent the drip chamber to atmosphere through said flexible tubing and hypodermic needle without fluid flowing through the flexible tubing and hypodermic needle;
   (c) when fluid in the drip chamber has reached a desired level, operating said control means to stop the drops from entering the drip chamber;
   (d) when said control means is operated to stop the drops from entering the drip chamber, operating said control means to stop the venting of the chamber and permit fluid in the chamber to flow out through the flexible tubing and the hypodermic needle until the fluid in the chamber is stabilized by a partial vacuum in the unvented chamber.

* * * * *